United States Patent [19]

Carlon

[11] 4,154,089
[45] May 15, 1979

[54] APPARATUS AND METHOD FOR MEASURING LIQUID WATER CONTENT OF A CLOUD OR FOG

[75] Inventor: Hugh R. Carlon, Bel Air, Md.

[73] Assignee: The United States of America as represented by the Secretary of the Army, Washington, D.C.

[21] Appl. No.: 914,830

[22] Filed: Jun. 12, 1978

[51] Int. Cl.² ............................................. G01N 21/34
[52] U.S. Cl. ........................................ 73/29; 250/343
[58] Field of Search ................. 73/29, 336.5; 250/338, 250/339, 340, 341, 343

[56] References Cited

U.S. PATENT DOCUMENTS

| 3,281,597 | 10/1966 | Greenberg | 250/343 |
| 3,636,768 | 1/1972 | Tinet et al. | 73/29 |
| 3,694,085 | 9/1972 | Rich | 73/29 |

*Primary Examiner*—Stephen A. Kreitman
*Attorney, Agent, or Firm*—Nathan Edelberg; A. Victor Erkkila; Max Yarmovsky

[57] ABSTRACT

An apparatus and method for measuring the liquid water content of a cloud or fog utilizes an environmentally controlled test chamber having a plurality of oppositely disposed windows selected to be optically transparent at a chosen wavelength of radiation. The windows of the chamber are positioned intermediate an infrared source and a wavelength scanning radiometer. An optical band pass filter is selected to pass radiation of a specific wavelength making the instrumentation substantially independent of cloud droplet size distribution enabling the measurement of only liquid water rather than water vapor.

12 Claims, 2 Drawing Figures

APPARATUS AND METHOD FOR MEASURING LIQUID WATER CONTENT OF A CLOUD OR FOG

GOVERNMENTAL INTEREST

The invention described herein may be manufactured, used and licensed by or for the Government for governmental purposes without the payment to me of any royalty thereon.

BACKGROUND OF THE INVENTION

Various means have been used in the prior art to determine the accurate measurement of total water content of an optical path through clouds or fog. The prior art meteorological devices frequently used rotating cylinders to sample air volumes, hot wires, collector heads, paper-tape impactors, and instrumentation measuring dew point and dielectric constants of the medium being sampled. The problem with some of the aforementioned apparatus was that it did not permit rapid and continuous monitoring of the liquid content of water in a cloud in a precise or reliable manner. In addition the prior art devices failed to operate where the cloud being sampled varied in concentration over a range of as much as 120 to 1 of both super cooled and normal droplets. The prior art methods and apparatus failed to give rapid response, caused disturbance of the sampled medium, would not lend themselves to easy calibration, were not rugged and reliable for aircraft use and did not give a continuous easily-interpreted output reading.

It is generally well known in the art that electromagnetic radiations may be attenuated by aerosole or droplets of fine particles and that extinction can be used to monitor aerosol concentration when particle sizes are known along with the complex indices of refraction of the medium. In the past measurements made at visible or near visible wavelengths have depended upon optical scattering arising from the "real" (refractive) part of the complex index. Because extinction with wavelength in the prior art devices was extremely dependent upon particle size and size distribution it has been necessary to measure these parameters and to correlate extinction readings with aerosol concentrations. The problem with these devices and methods was that errors were frequently large. At infrared wavelengths greater than 2.5 um, the "imaginary" (absorption) component of the complex index of refraction, for example of water, becomes an important factor. When the radiating wavelength is extended to the 8-13 um region, the region where normal atmospheric vapors do not absorb, approximately equal parts of total optical extinction are contributed by the "real" and "imaginary" components of water droplets. Thus, droplet size and size distribution must be first known before total optical extinction at these wavelengths can be used as a monitor of total aerosol concentration.

SUMMARY OF THE INVENTION

The present invention relates to an apparatus and method for rapidly and continuously measuring the liquid water content of clouds or fogs. The present invention utilizes a valved environmentally controlled chamber disposed intermediate a spectrally scanning radiometer with liquid nitrogen cooled detector, and a temperature controlled radiation infrared energy source.

An object of the present invention is to provide an apparatus and method for rapidly and continuously measuring the liquid content of a cloud or fog.

Another object of the present invention is to provide an apparatus and method for rapidly and continuously measuring the liquid content of a cloud or fog by use of a single-wavelength transmissometer operating in a specific critical wavelength in an atmospheric "window" region of the infrared radiation spectrum.

Another object of the present invention is to provide an apparatus and method for rapidly and continuously measuring the liquid water content of a cloud or fog at a critical wavelength which makes the operation of the apparatus substantially independent of droplet size distribution of the cloud.

Another object of the present invention is to provide an apparatus and method for continuously measuring the liquid content of a cloud while insuring little or no disturbance of the sampled medium.

Another object of the present invention is to provide an apparatus and method for continuously measuring the liquid water content of a cloud over a 100:1 concentration range of both supercooled and normal droplets.

A further object of the present invention is to provide an apparatus for continuously measuring the liquid water content of a cloud which lends itself to calibration and easily-interpreted output readings in $gm/m^3$.

For a better understanding of the present invention, together with other and further objects thereof, reference is made to the following descriptions taken in connection with the accompanying drawings.

DESCRIPTION OF THE PREFERRED EMBODIMENTS

Figure 1:
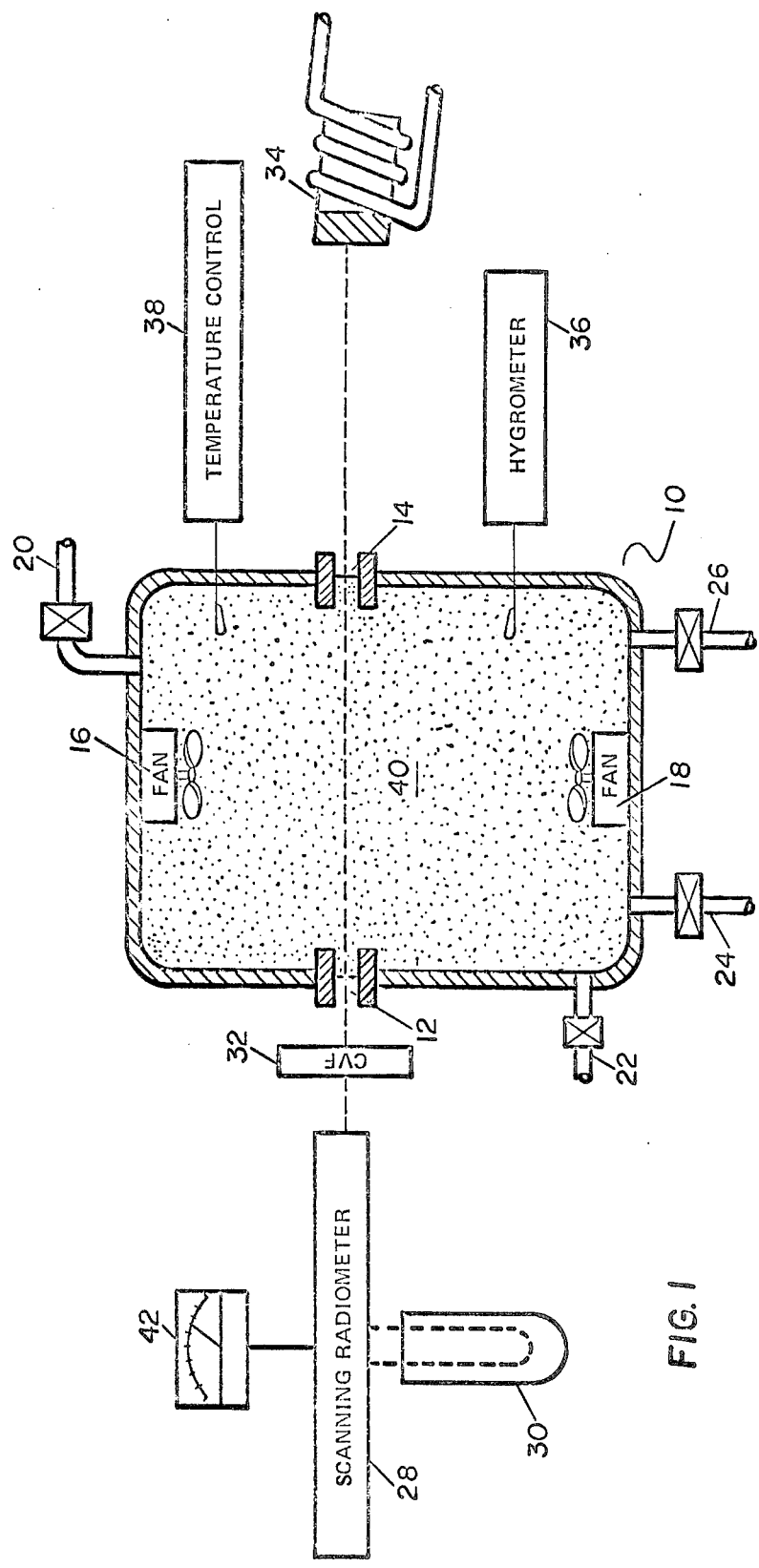
FIG. 1 is a partial cross-sectional schematic view of an apparatus for measuring the liquid water content of a cloud or fog created in an environmental test chamber.

Referring now to FIG. 1 a tubularly shaped environmental chamber 10 has a fifteen centimeter diameter first optically transparent window 12 positioned in one side of chamber 10 and a second optically transparent window 14 diametrically disposed in the opposite side of chamber 10 having an optical path length of 3.05 meters. The material of windows 10 and 12, chosen to be optically transparent at a selected critical wavelength of 11.5 um, is made of 0.0015 inch thick polyetheylene film. The window could be made of other materials such as Kodak "Irtran" series, KRS-5, fused salts or any other material or means such as circularly variable filter wheel as manufactured by Optical Cooling Laboratories, Inc., Santa Rosa, Calif., having optical transparency at a critically chosen wavelength which would allow transmission of an optical bandwith of approximately 2% of the center critical wavelength. Two electric fans 16 and 18 are operatively positioned on both ends of chamber 10 to maintain homogeneous aerosol concentrations during the testing procedure. Steam or the cloud or fog to be tested is introduced into the chamber 10 at top side via valved steam pipeline 20 and condensate may be exhausted therefrom at the end by valved pipeline drain 26. An exhaust pump or system not shown may be used to reduce chamber pressure through valve 22. Smoke or other type atmosphere may be introduced into the bottom end of chamber 10 by valved pipeline 24. Condensed liquids are drained from the bottom end of chamber 10 by drain line 26. A spectrally scanning radiometer 28, such as Exotech Model 10, infrared radiometer manufactured by Exotech, Inc., Gathersburg, Md., with its infrared detector modified to be cooled by a liquid nitrogen trap 30 is axially aligned and operatively disposed opposite to the first optically transparent window 12. A circular variable filter (CVF) 32 as aforesdescribed is positioned intermediate the scanning radiometer 28 and the first optically transparent window 12. A temperature controlled infrared energy source 34, such as model MS-153 black body manufactured by Electro-Optical Industries of Santa Barbara, Calif., is capable of generating radiations in the 3-5 um and 8-13 um wavelength region. Infrared energy source 34 is proximately disposed in alignment with the first and second optically transparent windows 12 and 14 respectively and in axial alignment with the wavelength selection filter 32 and scanning radiometer 28. The humidity and temperature of the chamber is determined and controlled by a hygrometer and a temperature controller 36 and 38 respectively each having its sensing elements operatively protruding through the chamber wall into the chamber 10.

Figure 2:
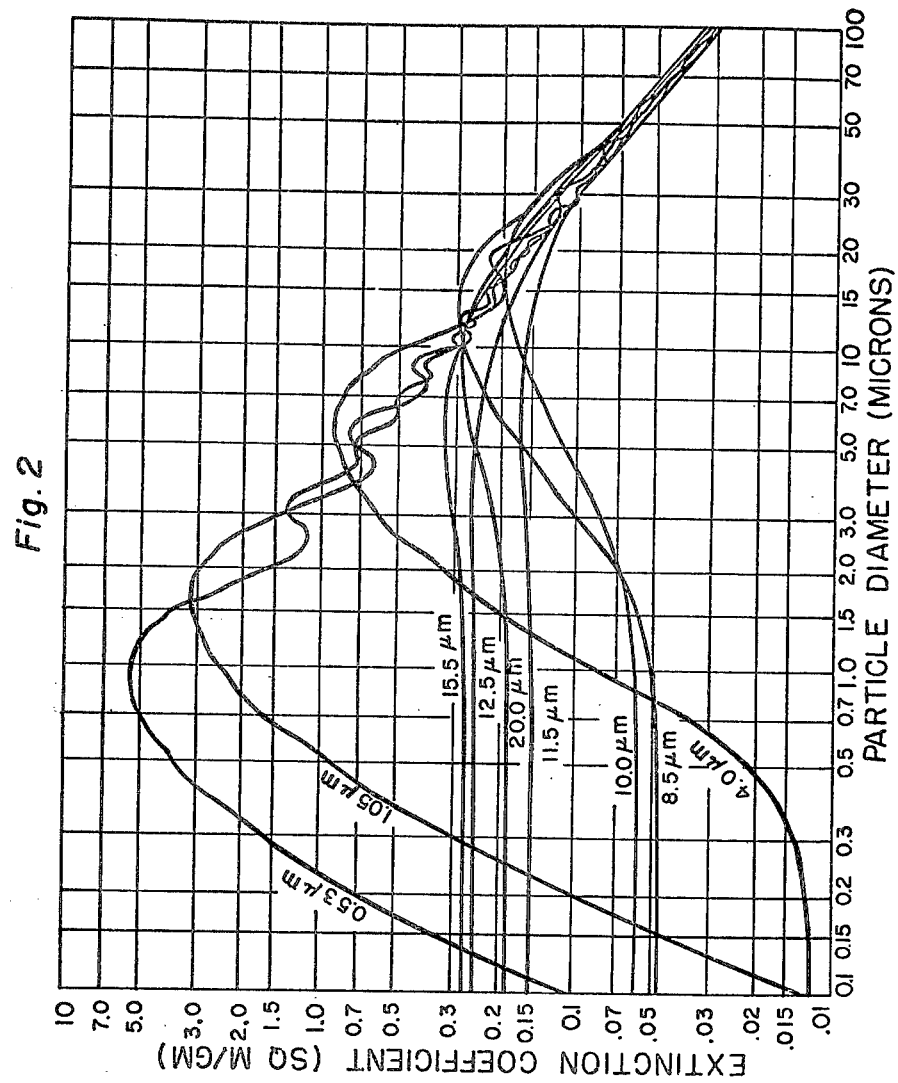
FIG. 2 is a plot of the total optical extinction versus droplet diameter for water for a variety of visible and infrared wave lengths.

Referring now to FIG. 2, plots of extinction coefficient in square meters per gram versus particle diameter in microns for various water droplets measured at various wavelength varying from the visible spectra to the infrared radiator on the apparatus as illustrated in FIG. 1. The various wavelengths of illumination are labeled upon the individual curves. It can be seen for the 0.53 um curve in the visible spectrum that the extinction coefficient has an extreme dependency upon particle diameter. At 0.53 um wavelength total extinction is virtually entirely due to "real index" scattering of the water droplets. As the wavelengths of illumination is increased, as shown on curves marked 1.05 um, 4.0 um, 8.5 um etc. the curves begin to flatten, with the peak or "hump" portions thereof flattening out toward the shorter droplet diameters. At the higher wavelengths of illumination reel index scattering, refraction, becomes unimportant when the droplet sizes fall well below illumination wavelengths. The curves approach a level determined, for smaller droplet sizes, by their "imaginary index" droplet absorption alone. It is also noticed that when the absorbing drops are small compared to the illuminating wavelength they behave almost as a gas, with no real-index scattering, with the important exception that the "gas" behaves according to the spectral characteristics of the aerosol material. The overall curve shapes at various wavelengths of illumination are thus seen to be dependent upon the shaping effects of the "real" (refractive) and "immaginary" (absorption) components of the complex index of refraction. It has been empirically determined using the apparatus of FIG. 1, that at or near a critical wavelength of 11.5 um illumination, because of the delicate balance between the refractive index contributions to curve shape at this precise wavelength, the instrumentation is virtually independent of droplet size number distribution over a very wide range of droplet sizes for water. From FIG. 2 we see that over the entire droplet diameter range of stable fogs and clouds of water, from droplets of less than 0.1 microns to droplets of more than 15 microns there is a variation of only approximately plus or minus 10% from a total extinction coefficient of 0.15 meters sq/gram for water clouds at the critical wavelength of 11.5 um.

In operation, calibration of the apparatus is accomplished by introducing a cloud of the type to be measured through either pipelines 20 or 24 into preheated chamber 10. Fans 16 and 18 are initiated to obtain a homogeneous mixture in chamber 18. The temperature controller 38 is adjusted to sustain saturation humidity. When the desired humidity is obtained on hygrometer 36 a homogeneous sample is drawn through exhaust pipeline 20 into a hygroscopic, preweighed sample tube or "gravimetric train," not shown, for determination of cloud concentration, typically in grams per cubic meter. At the same time, a signal generated by scanning radiometer 28 that was received from infrared source 34 through cloud 40 and circular variable filter 32 is monitored and compared to that obtained in the absence of any cloud. Knowing the ratio of the signals, the path length and droplet concentration at the critical infrared wavelength, the radiometer 28 is adjusted to give a scale setting on radiometer output meter 42 corresponding to the concentration of liquid of the cloud 40 in the sample volume using wellknown laws of optical extinction. As the cloud concentration varies, the radiometer output meter, calibrated in grams per cubic meter, will vary accurately indicating liquid water content. The critical wavelength of illumination for water was chosen at 11.5 um as shown in FIG. 2 for the reasons aforementioned.

The aforementioned method and apparatus is an example given for measuring the liquid content of a cloud for water, however the technique and apparatus are applicable to a wide variety of airborne droplet and aerosol materials provided that a suitable wavelength of illumination is selected or can be found to make operation of the instrument independent of droplet size and particle distribution.

The foregoing disclosure and drawings are merely illustrative of the principles of this invention and are not to be interpreted in a limiting sense. I wish it to be understood that I do not desire to be limited to the exact details of construction shown and described for obvious modifications will occur to a person skilled in the art.

Having thus fully described the invention, what is claimed as new and desired to be secured by Letters Patent of the United States is:

1. An apparatus for measuring liquid water content of a cloud or fog which comprises:

environmental chamber means for holding a sample of said cloud under condition of saturation humidity;

window means oppositely disposed and axially aligned in said environmental chamber adapted for optical transparency at a critical center wavelength of infrared radiation;

fan means operatively disposed in said environmental chamber for maintaining uniformity of droplet concentration therein;

valved pipe means for introducing a sample of said cloud into said environmental chamber and permitting a portion of said sample to be withdrawn therefrom for gravimetric measurement;

temperature-humidity control means operatively disposed in said environmental chamber for sustaining said sample under saturation humidity;

variable optical filter means, operatively disposed exterior to said chamber in axial alignment with said window means, said variable optical filter means providing for an optical bandwidth of approximately 2% of said critical wavelength of infrared radiation;

radiation means for generating infrared radiations at said critical wavelength; and scanning radiometer means in axial optical alignment with said variable optical filter means for detecting the refraction and absorption properties of said cloud to said critical wavelength infrared illumination and generating an output signal in response thereto, said output signal being calibrated in grams per cubic meter of liquid water contained in said sample.

2. An apparatus for measuring liquid water content of a cloud as recited in claim 1 wherein said window means comprises:

a first optical window, operatively disposed in one side of said chamber means, selected to be optically transparent at said critical wavelength;

a second optical window, operatively diametrically disposed in an opposite side of said chamber means, selected to be optically transparent at said critical wavelength.

3. An apparatus for measuring liquid water content of a cloud as recited in claim 2 wherein said first and second optical windows are made of 0.0015 inch polyetheylene film material.

4. An apparatus for measuring liquid water content of a cloud as recited in claim 3 wherein said valved pipe means includes a drain positioned in the bottom of said environmental chamber.

5. An apparatus for measuring liquid water content of a cloud as recited in claim 4 wherein said variable optical filter means includes a circular variable filter having 2% wavelength resolution of a critical center wavelength of 11.5 um.

6. An apparatus for measuring liquid water content of a cloud as recited in claim 5 wherein said scanning radiometer means includes means for liquid nitrogen cooling.

7. An apparatus for measuring liquid water content of a cloud as recited in claim 5 wherein said radiation means includes a temperature controlled infrared energy source capable of generating radiation in the 3-5 um and 8-13 um wavelength region.

8. A method for measuring the liquid content of a cloud or fog which comprises:

positioning a pair of optically transmissive windows in a chamber holding a cloud sample between said optically transmissive windows;

optically aligning a spectrally scanning radiometer with a first optical window of said optically transmissive windows;

positioning a circular variable filter intermediate said radiometer and said first optical window;

optically aligning an infrared energy source in front of a second window of said optically transmissive windows, said infrared source being in axial alignment with said first window, said circular variable filter and said radiometer;

preheating said cloud sample to a specified temperature;

introducing steam to obtain a cloud sample having a given droplet size and concentration;

cooling said cloud sample slowly to sustain saturation humidity;

blowing said cloud sample to maintain uniformity of droplet concentration;

maintaining said cloud sample at a specified temperature;

maintaining said cloud sample at a specified relative humidity;

measuring the radiometric emission signals from said cloud sample at a critical infrared wavelength wherein said radiometric emission signals are substantially independent of a droplet size distribution contained in said cloud sample; and calibrating said scanning radiometer to read the total liquid water content of said cloud sample in grams per cubic meter.

9. A method for measuring the liquid water content of said cloud sample as recited in claim 1 wherein the step of positioning said circular variable filter includes adjusting said variable filter to pass radiation within 2% of a critical wavelength of 11.5 um.

10. A method for measuring the liquid water content of said cloud sample as recited in claim 9 wherein the step of optically aligning said spectrally scanning radiometer includes cooling said radiometer with liquid nitrogen.

11. A method for measuring the liquid water content of said cloud sample as recited in claim 10 wherein the step of optically aligning said infrared energy source includes controlling the temperature of said infrared energy source.

12. A method for measuring the liquid water content of said cloud sample as recited in claim 11 wherein said step of controlling temperature of said infrared energy source includes regulating the flow of water in a water jacket to insure only emission signals recorded by said radiometer are only from said cloud sample.

* * * * *